April 11, 1950 J. S. KIRKLAND Plant Pat. 931
BOUGAINVILLEA PLANT
Filed Sept. 17, 1948
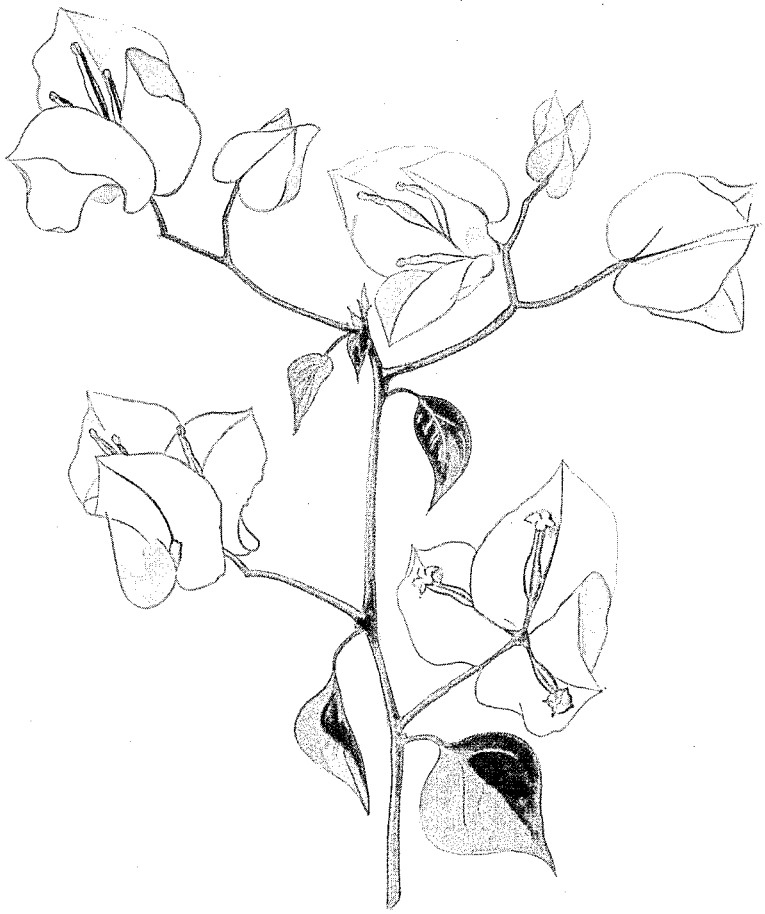
Joseph S. Kirkland
INVENTOR.
BY Farres & Filly
ATTORNEY Patented Apr. 11, 1950

Plant Pat. 931

UNITED STATES PATENT OFFICE

931

BOUGAINVILLEA PLANT

Joseph S. Kirkland, West Los Angeles, Calif.

Application September 17, 1948, Serial No. 49,690

1 Claim. (Cl. 47—60)

The present discovery relates to a new and distinct variety of bougainvillea plant, the original of which was a sport discovered by me in Los Angeles, California.

Cuttings from the original sport have been planted and exhibit all the characteristics of the original, including the distinctive color of the bracts, as hereinafter set forth. Additional cuttings have been taken from the asexually reproduced specimens just described, and the total number of living specimens now exceeds ten thousand, all of which exhibit the characteristics of the original.

The characteristics of the new variety as determined by careful observation since the discovery of the original sport in 1943 are specifically set forth hereinafter. The predominating attributes, however, which make this new variety of particular value as an ornamental vine are the distinctive yellow coloring and the persistence of the bracts.

As previously stated, this new variety of bougainvillea, the branch, foliage, bracts and blossoms of which are illustrated in the accompanying illustration, has been asexually reproduced and observations over the above stated period have determined that the characteristics are permanent. The original sport was a branch growing on a specimen of *Bougainvillea spectabilis* Willd. of the particular variety having bright red bracts and commonly designated as the Crimson Lake variety. The first cuttings to produce yellow bracts bloomed in 1944, the first distinctively colored bracts appearing in March and persisting until December.

As in *Bougainvillea spectabilis*, the blossoms proper in the new variety are small and inconspicuous, being a very faint pink in color. Upon first appearance from the leaf bud, the early bracts are a pinkish orange color, corresponding substantially to the Maerz and Paul Standard 10A6. As the bracts develop to maturity, the color develops through a light orange (10F7) to a bright lemon yellow, corresponding substantially to Maerz and Paul Standard 10L3.

The bracts are persistent during the entire maturing of the blossom, namely, from March until December (in Southern California).

When propagated in deep shade and in greenhouses, the bracts tend to be somewhat paler in color than when exposed to sunlight, although specimens regain their full yellow color upon exposure to sunlight.

The color of the foliage and stem ranges between Maerz and Paul Standard 23E6 and 23H4.

I claim:

A new and distinct variety of bougainvillea plant, characterized as to novelty by the size, persistence and yellow color of its bracts, substantially as shown and described.

JOSEPH S. KIRKLAND.

No references cited.